(12) United States Patent
Teicher et al.

(10) Patent No.: US 6,694,035 B1
(45) Date of Patent: Feb. 17, 2004

(54) SYSTEM FOR CONVEYING MUSICAL BEAT INFORMATION TO THE HEARING IMPAIRED

(76) Inventors: Martin Teicher, 40 Livingstone La., Waltham, MA (US) 02453; Steven Lowen, 19 Evelyn St., Burlington, MA (US) 01803

(*) Notice: Subject to any disclaimer, the term of this patent is extended or adjusted under 35 U.S.C. 154(b) by 195 days.

(21) Appl. No.: 09/899,733

(22) Filed: Jul. 5, 2001

(51) Int. Cl.[7] .............................................. H04R 25/00
(52) U.S. Cl. ....................... 381/326; 381/151; 381/312; 381/380; 601/47
(58) Field of Search ................................ 381/312, 326, 381/380, 151; 600/26, 27, 28; 601/46, 47

(56) References Cited

U.S. PATENT DOCUMENTS

| | | | |
|---|---|---|---|
| 3,958,486 A | 5/1976 | Sears | |
| 4,354,064 A * | 10/1982 | Scott | 381/326 |
| 4,908,869 A | 3/1990 | Lederman | |
| 5,734,731 A * | 3/1998 | Marx | 381/119 |
| 6,104,820 A * | 8/2000 | Soza | 381/151 |
| 6,173,058 B1 * | 1/2001 | Takada | 381/66 |

* cited by examiner

*Primary Examiner*—Curtis Kuntz
*Assistant Examiner*—Tuân Dúc Nguyên
(74) *Attorney, Agent, or Firm*—Daly, Crowley & Mofford, LLP.

(57) ABSTRACT

A beat detection system provides tactile stimulation in response to musical characteristics and in particular to repetitive musical beat information. The device processes multiple acoustic bands and separates out the beat information from each band. Each band provides beat information to respective tactile mechanisms that convey the beat information to the user. The device can be worn by a person with a hearing disability to enable them to appreciate the beat of music.

25 Claims, 4 Drawing Sheets

SYSTEM FOR CONVEYING MUSICAL BEAT INFORMATION TO THE HEARING IMPAIRED

CROSS REFERENCE TO RELATED APPLICATIONS

Not Applicable.

STATEMENT REGARDING FEDERALLY SPONSORED RESEARCH

Not Applicable.

FIELD OF THE INVENTION

The present invention relates generally to hearing prostheses and, more particularly, to systems for providing musical beat information to the hearing impaired.

BACKGROUND OF THE INVENTION

In general, people with a hearing impairment like to participate in activities and social occasions in a manner similar to people without hearing loss. As is known in the art, there are a variety of conventional prostheses to assist people with varying degrees of hearing loss. Most hearing aids are useful to people with a slight to moderate hearing loss. More aggressive approaches are also known in the art, such as cochlear inner ear implants, for helping those with more severe hearing. Cochlear implants can help a person with damaged cochleae but with viable nerves running from the cochleae to the brain. Even more aggressive approaches are known, such as brain stem implants, that include systems for transmitting sound information directly to the brain stem, bypassing damaged cochlear nerves.

Typical hearing aids do not help those with a severe hearing impairment, and implants require expensive equipment, as well as delicate surgery or series of surgeries, which may not provide satisfactory results. Many people with uncorrected severe hearing loss would enjoy the ability to appreciate musical beat information. In particular, those with severe or total hearing loss would appreciate the ability to sense the beat of music, thereby enabling them to dance at social functions and the like.

Those of ordinary skill in the art understand the beat of music to be the repetitive change in signal intensity or amplitude within some part of the total acoustic frequency spectrum of the music. The beat information may be located in different parts of the spectrum for different music. For example, the beat may be a repetitive beat of a bass drum, with spectral characteristics dominating the lower end of a total acoustic music spectrum. Alternatively, the beat of the music may be dominated by a repetitive change in amplitude at a higher frequency part of the spectrum. For example, an orchestral piece may contain a repetitive sound from a violin, with spectral characteristics dominating a higher frequency part of the total music acoustic spectrum.

U.S. Pat. No. 3,958,486 to Sears, entitled Keyboard Attachments, discloses a hearing prosthesis having a direct electrical connection between a keyboard and indicator lights. The keyboard device provides a visual indication of the music played on the keyboard.

U.S. Pat. No. 4,908,869 to Ledermen, entitled Induction-Based Assistive Listening System, discloses a hearing prosthesis for inducing electromagnetic signals into existing hearing aids. The Lederman device can communicate to hearing aids without sound, thus providing non-acoustic communication.

U.S. Pat. No. 4,354,064 to Scott, entitled Vibratory Aid for Presbycusis, discloses a hearing prosthesis-that provides a tactile output in response to sound energy. The Scott device provides a tactile representation of the high frequency components of either speech or music.

While these devices can overcome hearing loss, such devices do not enable a person with a severe hearing loss to easily enjoy musical beat information. It would, therefore, be desirable to provide a system for providing musical beat information to those having severe hearing impairment.

SUMMARY OF THE INVENTION

The present invention provides a system for conveying musical beat information via tactile representation. With this arrangement, a person, particularly a person with severe or total hearing impairment, can perceive musical beat information so as to enable that person to dance. While the invention is primarily shown and described in conjunction with conveying musical beat information, it is understood that the invention is applicable to other systems in which it is desirable to provide a tactile representation of an audio signal.

In one aspect of the invention, a system for conveying musical beat information includes a sound detector for receiving music and providing a signal corresponding to the music to an audio processing unit. The audio processing unit generates one or more electrical outputs to tactile actuators for conveying a tactile representation of the beat information to a user. With this arrangement, a tactile output is provided in response to the musical beat so that a person with severe or total hearing impairment can sense a musical beat.

In a further aspect of the invention, the audio processing unit contains one or more electronic filters for selecting corresponding audio frequency bands. The audio processing unit provides one or more band-selected electrical outputs to tactile actuators, where the band-selected outputs correspond to the filter frequency bands. In one embodiment, each tactile actuator is responsive to the beat within a particular audio frequency band.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
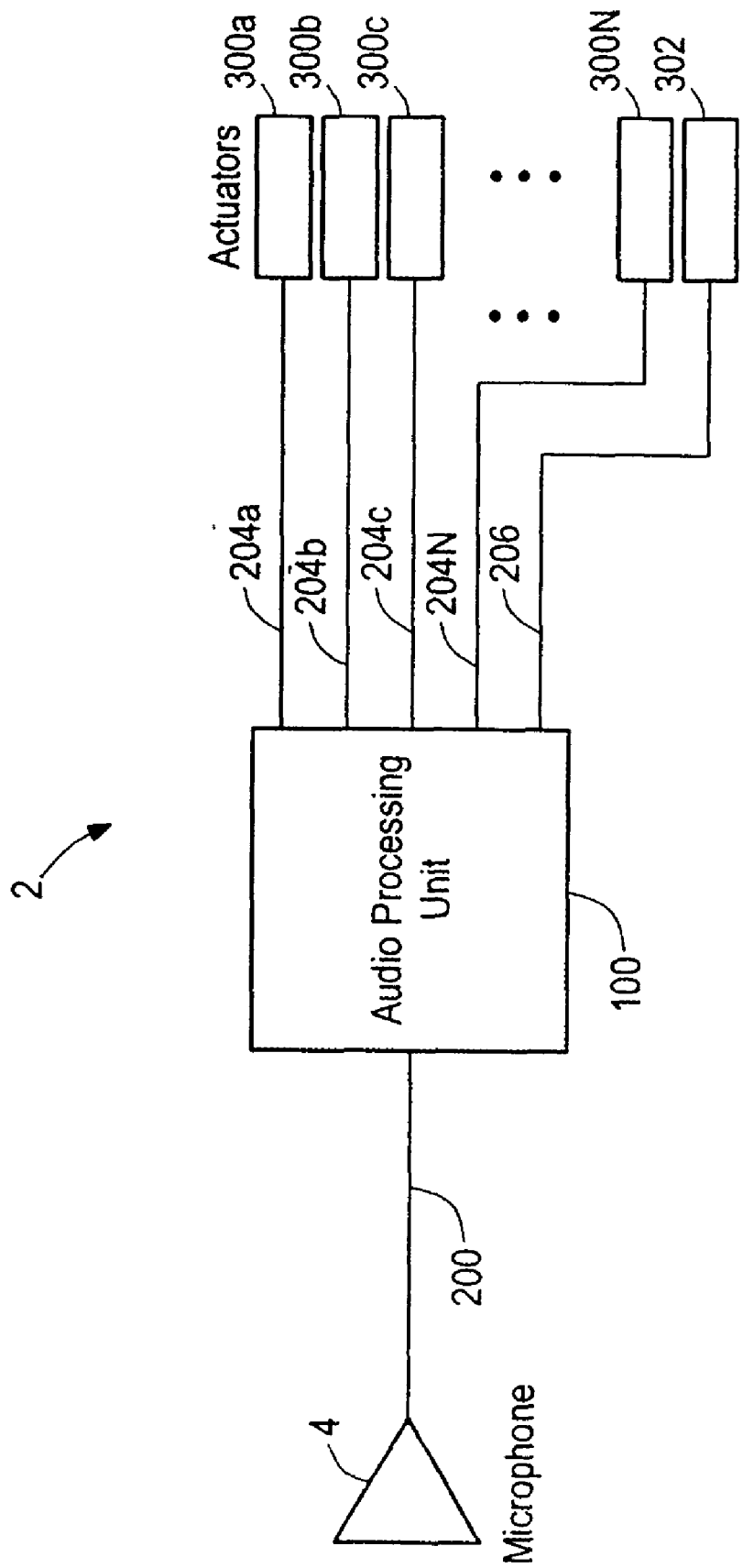
FIG. 1 is a top level block diagram of a system for conveying musical beat information in accordance with the present invention.

FIG. 1 shows an exemplary system 2 for conveying musical beat information to a user in accordance with the present invention. The system 2 includes a sound detector, such as a microphone 4, an audio processing unit (APU) 100, and a series of tactile actuators 300a–N, 302. The microphone 4, which is an audio transducer, is used to convert sound energy into electrical energy. It will be readily apparent to one of ordinary skill in the art that a variety of microphones can be used to provide electrical signals to the APU 100. Exemplary sound detectors include diaphragm/coil and piezoelectric type microphones.

The microphone 4 provides an electrical signal 200 to the APU 100. The APU 100 processes the electrical signal 200 from the microphone 4 and provides one or more output signals 204*a*–N, 206 to respective tactile actuators 300*a*–N, 302. In general, the tactile actuators 300*a*–N, 302 impart tactile sensation to the skin of a person using the invention.

It is understood that the tactile actuators 300*a*–N, 302 can be of various constructions and techniques. Exemplary tactile actuators include vibratory and solenoid type devices. One of ordinary skill in the art will recognize that a wide range of tactile actuators can be used to provide tactile sensation to the user, including vibrating devices, tapping devices, devices that move over the skin, and devices that vary pressure against the skin slowly. It will also be recognized by one skilled in the art that visible lights may be used in place of the tactile actuators to convey the musical beat information to a user.

The illustrative embodiment of FIG. 1 describes an embodiment having five tactile actuators 300*a*–N, 302, each of which provides a corresponding tactile sensation to the user. It will be appreciated that fewer than five or more than five tactile actuators can be used without departing from the present invention. In the illustrated embodiment, the five tactile actuators allow the user to distinguish five different tactile sensations, each representing different beat information.

Figure 2:
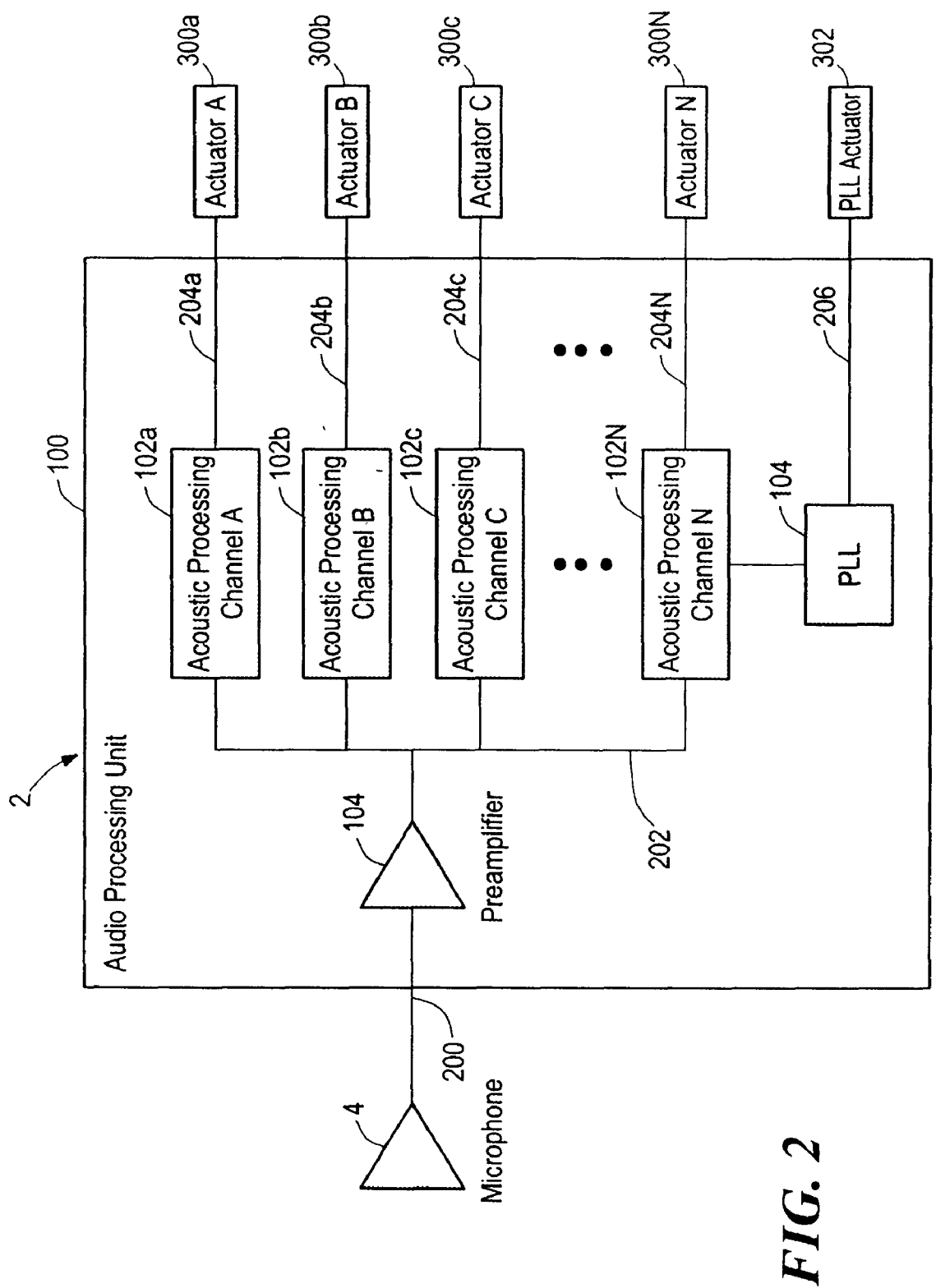
FIG. 2 is a block diagram of an audio processing unit that can form a part of the system of FIG. 1.

FIG. 2 shows an exemplary embodiment of the APU 100 of FIG. 1, in which like reference numbers indicate like elements. The APU 100 has multiple parallel processing channels 102*a*–N. Each processing channel 102*a*–N operates upon a selected band of the total bandwidth of the electrical signal 202 from the microphone preamplifier 104. It is understood that each of the processing channels 102*a*–N can be of similar construction, differing only in the electrical bandwidth which each processes.

In general, each of the plurality of processing channels cover respective frequency bands since it is not known apriori in which acoustic band or bands the musical beat information will be found. For example, the beat information may dominate at relatively low frequencies, which can correspond to the beat of a drum for example. Alternatively, the beat information may dominate at relatively high frequencies, which can correspond to the repetitive tones of a clarinet, for example. Thus, the system 2 employs multiple acoustic processing channels 102*a*–N in parallel. Each such processing channel 102*a*–N employs a unique band pass filter 106*a*–N for processing the beat information of the spectral band that relates to its particular band pass filter 106*a*–N.

In one embodiment, the APU 100 includes an optional phase locked loop (PLL) 104 in communication with one of the processing channels 102N. In response to beat information, the PLL 104 sends a repetitive signal to the fifth tactile actuator 302. The repetitive PLL signal 104 has different characteristics than acoustic processing channel output signals 102*a*–N in that it greatly reduces any fluctuations in beat-to-beat timing, yielding a more periodic and likely truer representation of the beat itself. It should be recognized by one of ordinary skill in the art that other embodiments can have additional PLLs connected to any or all of the processing channels 102*a*–N.

Figure 3:
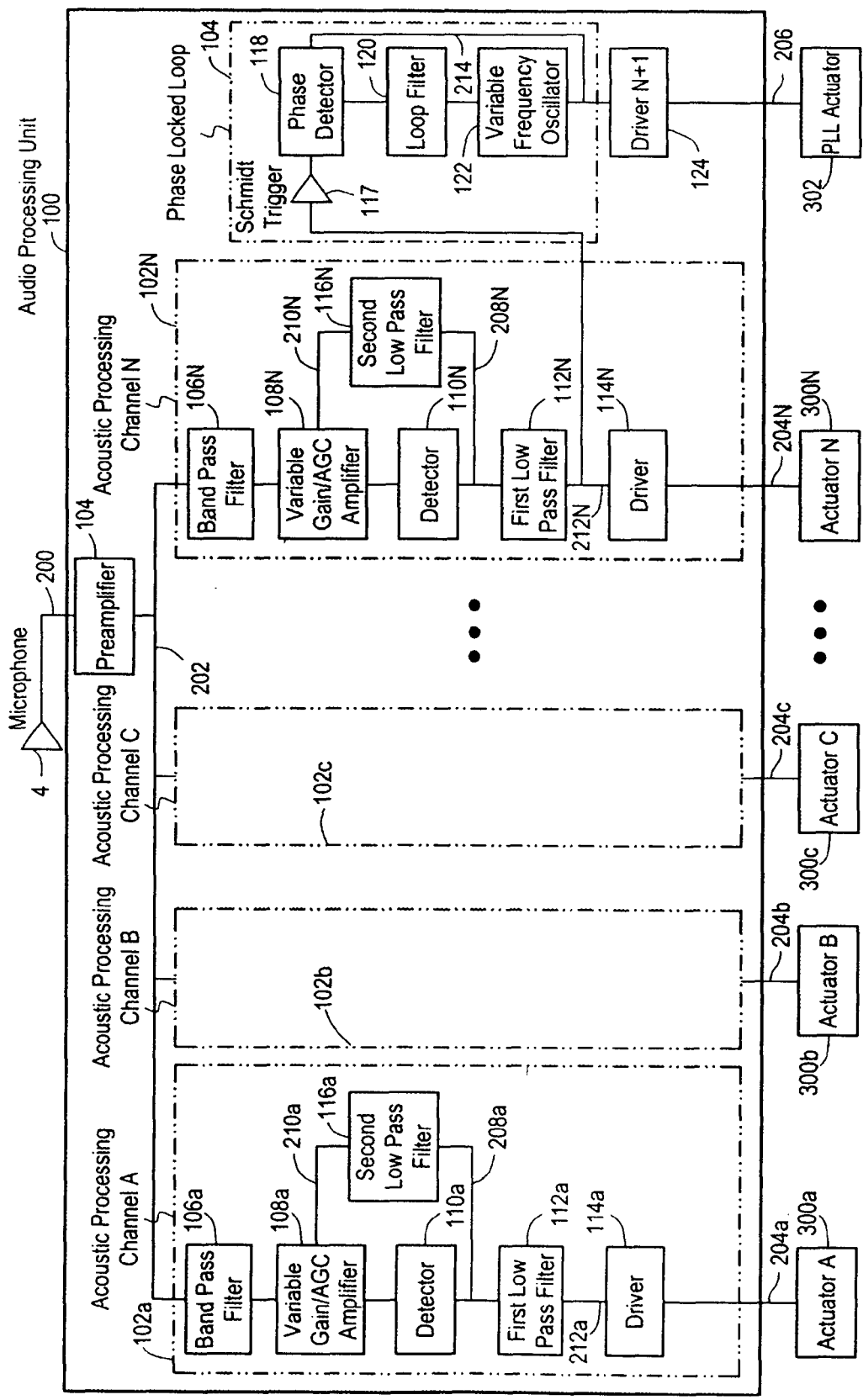
FIG. 3 is a block diagram showing an exemplary implementation of the system of FIG. 1.

FIG. 3 shows an exemplary implementation of the APU 100 of FIG. 2. The acoustic processing channels 102*a*–N of the APU 100 each receive an input signal 202 from the microphone preamplifier 104 corresponding to the music. It is understood that the channel A acoustic processing channel 102*a* is representative of the other channels 102*b*–N of the unit. The signal 202 from the preamplifier 104 is provided to the channel A band pass filter 106*a*.

Exemplary frequency bands of band pass filters 106*a*–N for the acoustic processing channels 102*a*–N are in Table 1.

TABLE 1

| Band Pass Filter a–N | Minimum Frequency (Hz) | Maximum Frequency (Hz) |
| --- | --- | --- |
| Channel A | 20 | 100 |
| Channel B | 100 | 500 |
| Channel C | 500 | 2,000 |
| ..... | ..... | ...... |
| Channel N | 2,000 | 20,000 |

It will be recognized by one skilled in the art, that other bands of interest may be used without departing from the invention. It will also be recognized by one skilled in the art that the band pass filter bands can overlap.

The output of the channel A band pass filter 106*a* is provided to the channel A variable gain amplifier 108*a* which provides automatic gain control (AGC) in conjunction with signal magnitude feed back 210*a* from the channel A second low pass filter 116*a*. It should be noted that the AGC feedback via the channel A second low pass filter 116*a* is a slowly varying control signal. Depending upon the filter characteristics of the channel A second low pass filter 116*a*, the gain of the channel A AGC amplifier 106*a* can vary rapidly or slowly in response to varying signal amplitudes. In one embodiment, the channel A second low pass filter 116*a* has a low cutoff frequency corresponding to a time constant of about one second, thus creating an AGC with a relatively slowly varying gain.

The signal from the channel A AGC amplifier 106*a* is provided to the channel A detector/filter pair, which includes a detector 110*a* and a first low pass filter 112*a*. Detector/filter circuits for detecting lower frequency amplitude fluctuations of a higher frequency carrier signal are well known to one of ordinary skill in the art. Such a detector is commonly used as the audio signal detector in an amplitude modulated (AM) radio receiver, for example.

Those of ordinary skill in the art will appreciate that the detector/filter function can be achieved using a variety of techniques. For example, the detector can include a full-wave or half-wave rectifier, with or without additional active devices, absolute value circuit, square-law device, or other memory-less non-linearity, each of which has many known configurations. Furthermore, the low pass filter of the pair can be achieved using many known techniques, such as resistor and capacitor networks, alone or in conjunction with active devices.

In an exemplary embodiment, the detector 110*a* and the filter 112*a* employ diodes, resistors, and operational amplifiers for the detector and resistors, capacitors, and operational amplifiers for the filter.

The output signal 212*a* from the channel A first low pass filter 112*a* is representative of the amplitude fluctuations of the original signal 202. It is understood that the original signal 202 is a composite signal, representative of the original acoustic energy, with complex frequency and time characteristics. In contrast the channel A signal 212*a* is a reduced bandwidth signal, band-limited by the channel A band pass filter 106*a*. If the signal 212*a* contains signal characteristics where the fluctuations are rhythmic and repetitive, the fluctuations represent the beat of the music. If the signal 212a does not contain repetitive characteristics, another of the filter output signals 212a–N, each representing a different acoustic frequency band, will likely contain repetitive characteristics. Thus, beat information is obtained at one or more of the outputs 204a–N from the APU.

In one embodiment, the channel A first low pass filter 112a has a time constant, $\tau$, of about 40 milliseconds, corresponding to maximum practical beat frequency of about $1/(2\pi\tau)$ or 4 Hz. However, those familiar with the art will recognize that other time constants would be possible without departing from the spirit of this invention. Time constants representing beat frequencies in the range of 0.1 to 10 Hz are easily realizable. Frequencies in this range are readily recognizable as beat information through tactile means, although beat frequencies range from perhaps 0.25 to 4 Hz in the majority of cases.

The beat information signal 212a is then passed through the channel A driver 114a which converts the low power (low voltage and low current) signal 212a to a higher power signal 204a. The higher power signal 204a is sent out of the APU 100 to a channel A tactile actuator 300a. Each output signal 204a–N and corresponding tactile actuator 300a–N indicates beat information from different regions of the overall complex acoustic frequency spectrum.

As described above, the APU can include one or more phase locked loops for providing more precise beat information. Although the illustrative embodiment of FIG. 3 shows a single PLL 104, it is understood that more and fewer PLLs can be used.

The PLL 104, which receives the output 212N of the channel N first low pass filter 112N with a Schmidt trigger 117, can be used to detect low frequency repetitive signal content of the band pass input signal 106N. Alternatively, the phase locked loop can receive the output of the preamplifier 202 with the Schmidt trigger 117 if a separate detector and low-pass filter are provided between them.

Phase-locked loops are well known to those skilled in the art. In general, the PLL operates with a long time constant to keep the phase and frequency of the PLL output signal 214 equal to the time-averaged input phase and frequency of the input signal 212N.

In one particular embodiment, the PLL 104 includes a Type 2 phase detector 118, a loop filter 120, and a variable frequency oscillator 122. Input signal 212N is phase-compared to PLL output signal 214. The loop characteristics of the PLL are designed to keep the PLL output signal 214 in average phase relationship with the input signal 212N. When this condition is achieved, the PLL is said to be locked.

In operation, phase and frequency fluctuations of the input signal 212N are effectively removed to create an average phase and frequency signal 214 with slowly varying characteristics in response to the average phase and frequency of the input 212N. Thus, the PLL output signal 214 is a repetitive signal, relatively constant in frequency and amplitude. This is in contrast to the other output signals 212a–N that vary in frequency and amplitude. The PLL circuit is thus used to give a further indication of the musical beat. The PLL output signal 214 is a constant amplitude repetitive AC signal that corresponds to the musical beat.

It is understood that the PLL dynamic characteristics are determined by the characteristics of the phase detector 118, loop filter 120, and the variable frequency oscillator (VFO) 122. One skilled in the art will recognize that a variety of phase detectors, loop filters and variable frequency oscillators suitable for this application can be used.

While the exemplary embodiment shown has one PLL, it should be recognized that other numbers of PLLs and associated tactile actuators, in communication with other of the acoustic processing channels 102a–N, may be employed without departing from the invention. Each may have different time constants or topologies.

Figure 4:
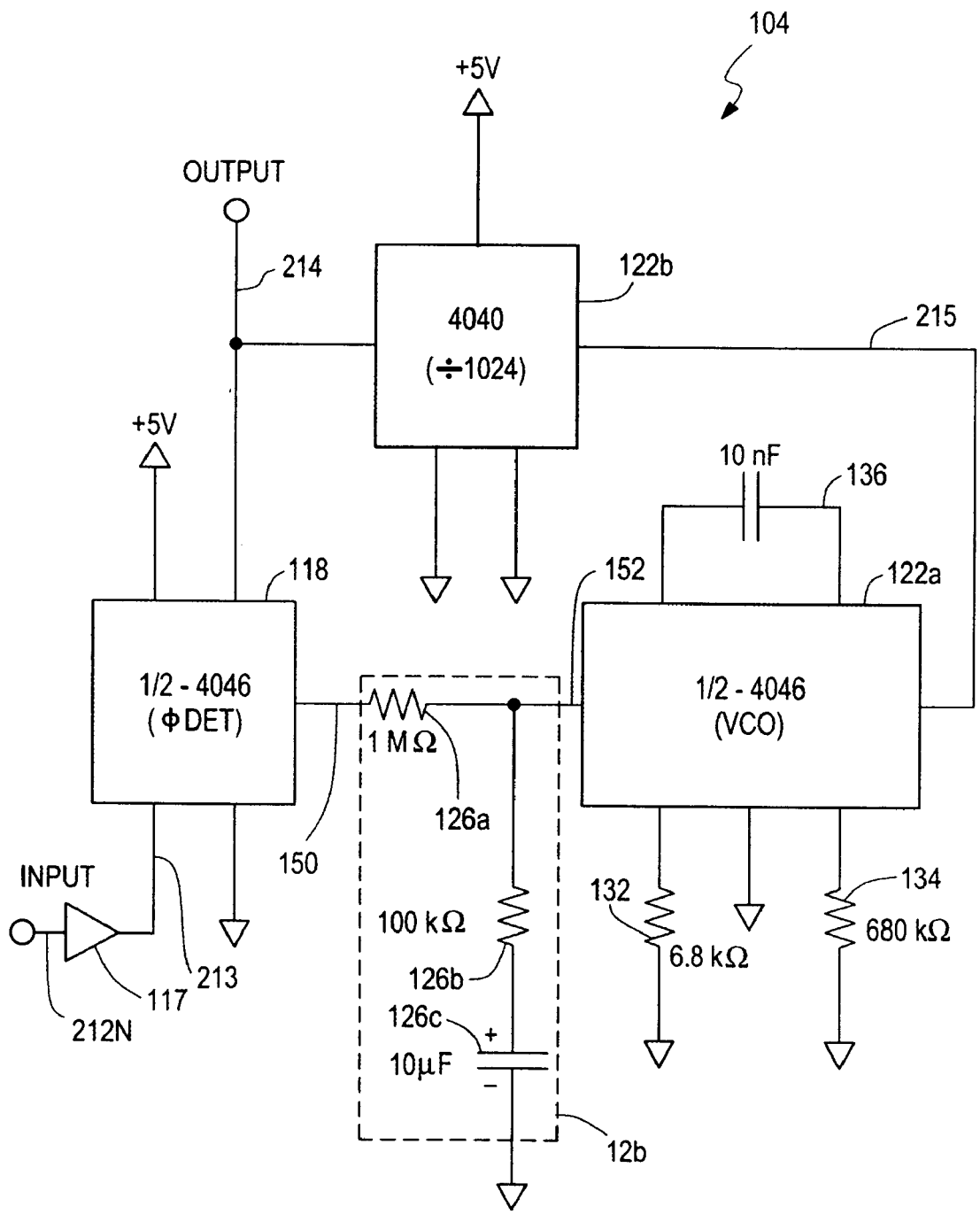
FIG. 4 is a block diagram showing an exemplary implementation of the phase locked loop that forms part of the system of FIGS. 2 and 3.

FIG. 4 shows a schematic of an exemplary implemention of a phase locked loop 104 that can be used as part of this invention. The phase locked loop design 104 is based upon a conventional 4046 integrated phase locked loop device 118, 122a. As known to one skilled in the art, 4046 refers to a commonly available generic phase locked loop integrated circuit. The 4046 device contains the type 2 phase detector 118 and a voltage controlled oscillator 122a.

The input signal 212N from the channel N first low pass filter 112N is presented to a Schmidt trigger device 117. A Schmidt trigger device is known to one skilled in the art to provide an amplified square wave output 213 from an analog input 212N. Here, the input 212N is an analog waveform representing the beat of the music. The Schmidt trigger output 213 is an amplified signal that will take two states, either high or low, depending upon whether the input 212N is above a first voltage threshold or below a second voltage threshold. The use of the Schmidt trigger 117 is particular to the phase locked loop implementation shown herein, where the Type 2 phase detector 118 of the 4046 device 118, 122a requires a square wave input for proper operation.

The phase detector output 150 is presented to a loop filter 126 that provides a filtered signal 152 to the input of a variable frequency oscillator 122. Loop filter 126 characteristics are determined by the value of associated components 122a–c. The variable frequency oscillator 122 is composed of the voltage controlled oscillator (VCO) 122a and a divider 122b, a divide by 1024 device. The indicated 4040 device 122b represents the generic part. number of one type of digital divider among many types of commonly available suitable digital dividers. Together, the VCO 122a and divider 122b provide a PLL output signal 214 in response to the filtered signal 152. The relationship between the voltage 152 and the frequency of the PLL output signal 214 is related to the value of capacitor 136 and resistors 132, 134.

The type 2 phase detector 118 produces a voltage output that corresponds to the phase difference between the input signal 212N and the PLL output signal 214. Feedback from the PLL output signal 214 to the phase detector 118 operates to keep the input signal 212N and the PLL output signal 214 substantially in an average phase relationship as mentioned earlier.

One skilled in the art will realize that there are many design parameters associated with a phase locked loop. Two PLL parameters include the lock range and the hold range. The lock range represents the range of input frequencies over which the PLL can acquire the lock condition. Once locked, the hold range represents the range of input frequencies over which the loop can remain locked. Type 1 phase detectors are generally limited to capture ranges of perhaps +–30%, far too narrow for the 0.1 to 10 Hz range desired. Therefore a Type 2 detector is preferred, which has can easily function over a 1:1000 range of frequencies. A type 2 phase detector also has the advantage that in the locked state the PLL output 214 will be precisely in-phase with input 212N that represents the beat, while Type 1 detectors will yield outputs that typically lead or lag the beat. However, for situations when the beat is known to be in a relatively narrow range (such as in some dance music), a Type 1 detector can be employed. This has the advantage of greater noise immunity, and can be connected to the output 208N of the detector 110N directly without filtering.

It will be recognized to one skilled in the art that other PLL topologies and schematic designs with additional time constants and/or nonlinearities can be employed in this invention.

One skilled in the art will appreciate that various elements of the APU can achieved by different techniques, such as digital techniques, without departing from the present invention. For example, the band pass filters 106a–N, the AGC amplifiers 108a–N, the detectors 110a–N, and the first low pass filters 112a–N, can be digitally implemented. One of ordinary skill in the art will recognize a digital band pass filter could be implemented by using a fast Fourier transform (FFT) mathematical technique. Once converted to a digital signal with a standard analog to digital converter (A/D), also commonly known in the art, the entire composite time domain signal can be converted to a frequency domain spectral representation by performing an FFT. Selected bands of this frequency spectrum representation can be separated from other digital data to yield a band pass function. An inverse FFT process can then regenerate a time domain representation of the band passed signal. One skilled in the art will recognize other digital techniques for implementation of a digital band pass filter, including FIR and IIR filter designs and/or wavelet decomposition. One skilled in the art will also recognize that the digital band pass filter can be replaced with a digital Kalman filter.

The AGC 108a–N can also be digitally implemented. The magnitude can be digitally detected by processing the digital values from the A/D converter. A desired scaling factor can be determined and used to scale the digital values. Techniques known in the art can multiply or divide the digital signal data values by the scaling factor. Thus, an AGC amplifier can be implemented digitally.

The detector 110a–N and first low pass filter 112a–N functions can also be digitally implemented. Once the signal is converted from an analog signal to a digital signal with an analog to digital converter, (A/D), digitally band pass filtered and amplified as above, the detector can be performed with a simple mathematical absolute value function upon the sampled digital values. The low pass filter 112a–N can also be achieved digitally with well known techniques including finite impulse response (FIR) and infinite impulse response (IIR) filters.

One of ordinary skill in the art will also recognize that the PLL 104 can also be digitally implemented whereby the loop filter 126 and VCO 122a are provided using digital techniques.

One skilled in the art will recognize that digital implementations allow more sophisticated processing techniques to be employed. Such techniques include neural networks that can allow a hearing person to first 'teach' the system of this invention. Such techniques also include pre-selection by the user of the type of beat to expect, for example, a waltz.

One skilled in the art will recognize that any or all of the aforementioned electronic circuitry can be integrated into custom integrated circuits.

In an exemplary embodiment, the beat detection system is portably mounted to the user. In alternative embodiments, one or more of the elements of the invention are stationarily mounted. In further embodiments, the system includes a central processing station, for example a stationary APU connected to a stationary radio transmitter that broadcasts beat information to a radio receiver and tactile actuator sets mounted to the user. In further embodiments, the system includes a stationary radio transmitter that broadcasts music to a radio receiver, APU, and tactile actuator sets mounted to the user. In other embodiments, the APU can be directly connected to a stereo or other receiver. In still other embodiments, visible lights can provide the beat information.

One of ordinary skill in the arts will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for conveying musical beat information, comprising:
   a sound detector for receiving music and generating a music output signal;
   an audio processing unit responsive to the music output signal for providing a beat information output signal, wherein the audio processing unit includes a first amplifier which receives the music output signal and outputs a pre-amplified music signal, and wherein the audio processing unit includes a plurality of channels, wherein a first one of the plurality of channels includes a band pass filter in communication with the first amplifier for passing a predetermined frequency range;
   at least one sensory device responsive to the beat information output signal for providing a sensory representation of beat information contained in the beat information output signal; and
   a radio transmitter connected to the first amplifier and a radio receiver connected to the band pass filter for radio communication of the pre-amplified music signal to the band pass filter.

2. The system according to claim 1, wherein the sound detector is a microphone.

3. The system according to claim 1 wherein the first one of the plurality of channels further includes a second amplifier coupled to the band pass filter for automatic gain control.

4. The system according to claim 3 wherein the first one of the plurality of channels further includes a detector coupled to the second amplifier for amplitude modulation detection.

5. The system according to claim 4 wherein the first one of the plurality of channels further includes a first low pass filter coupled to the detector for additional amplitude modulation detection.

6. The system according to claim 5 wherein the first one of the plurality of channels further includes a power amplifier driver coupled to the first low pass filter.

7. The system according to claim 6 wherein the first one of the plurality of channels further includes a second low pass filter coupled to the detector and coupled to the second amplifier for automatic gain control feedback.

8. The system according to claim 7 wherein at least one of the plurality of channels is analog.

9. The system according to claim 7 wherein at least one of the plurality of channels is digital.

10. The system according to claim 7 wherein the first one of the plurality of channels further comprises a phase locked loop coupled to the output of the first low pass filter.

11. A system according to claim 1 wherein the at least one sensory device includes a tactile actuator.

12. The system according to claim 1 wherein the at least one sensory device includes a vibrating device.

13. The system according to claim 1 wherein at least one of the sensory devices includes a visible light.

14. The system according to claim 1, wherein the audio processing unit includes a plurality of channels each corresponding to a respective frequency band.

15. The system according to claim 1, wherein the at least one sensory device includes a plurality of tactile actuators coupled to respective ones of the plurality of channels such that each tactile actuator conveys beat information in the corresponding frequency band.

16. A method for conveying musical beat information, comprising:

receiving music;

generating a music output signal corresponding to the music;

processing the music output signal with an audio processing unit to provide a plurality of beat information output signals, wherein the audio processing unit includes a first amplifier for receiving the music output signal to produce a pre-amplified music signal, wherein processing the music output includes filtering the pre-amplified music signal to produce a second signal;

amplifying the second signal with a second amplifier to produce a third signal;

detecting the third signal to produce a fourth signal;

filtering the fourth signal to produce a fifth signal;

filtering the fourth signal to produce a sixth signal; and relating sixth signal to the second amplifier to control the gain of the second amplifier; and power amplifying the fifth signal to produce the beat information output signal; and providing a sensory representation of beat information contained in the plurality of beat information output signals to a user.

17. The method according to claim 16, further including receiving the music with a microphone.

18. The method according to claim 16, further including a radio transmitter and a radio receiver for communication of the second signal to the second amplifier.

19. The method according to claim 18, further including amplifying, detecting, filtering, and relating in analog format.

20. The method according to claim 18, further including amplifying, detecting, filtering, and relating in digital format.

21. The method according to claim 18 further including processing the music output signal by phase detecting with a phase locked loop coupled to the fifth signal to provide the beat information output signal.

22. The method according to claim 16 further including providing the sensory representation with a tactile actuator.

23. The method according to claim 16 wherein the step of providing a sensory representation is done with at least one tactile actuator which is a vibrating device.

24. The method according to claim 16 wherein step of providing a sensory representation is done with at least one visible light.

25. The method according to claim 16, further including processing the music output signal with a Kalman filter.

* * * * *